United States Patent
Vetter

(10) Patent No.: US 8,805,468 B2
(45) Date of Patent: *Aug. 12, 2014

(54) GUIDE TUBE FOR AN IMPLANTABLE DEVICE SYSTEM

(75) Inventor: Rio J. Vetter, Augusta, MI (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/491,358

(22) Filed: Jun. 7, 2012

(65) Prior Publication Data

US 2012/0316417 A1    Dec. 13, 2012

Related U.S. Application Data

(63) Continuation of application No. 12/253,796, filed on Oct. 17, 2008, now Pat. No. 8,224,417.

(60) Provisional application No. 60/980,650, filed on Oct. 17, 2007.

(51) Int. Cl.
  *A61B 5/0478* (2006.01)
  *A61N 1/36* (2006.01)
  *A61N 1/05* (2006.01)

(52) U.S. Cl.
  CPC .......... *A61N 1/0534* (2013.01); *A61N 1/0551* (2013.01); *A61N 1/36082* (2013.01)
  USPC .......... 600/378; 600/377; 600/544; 607/116

(58) Field of Classification Search
  CPC .......... A61B 1/00154; A61B 5/04001; A61B 5/0478; A61B 5/40; A61B 5/4058; A61B 5/4064; A61B 5/4076–5/4094; A61B 5/6847; A61B 5/6868; A61B 2017/00831; A61B 2017/00862; A61B 17/3415; A61B 17/3417; A61B 17/3439; A61B 17/3468; A61B 2560/06; A61B 2560/063; A61B 2560/066; A61N 1/0529; A61N 1/0531; A61N 1/0534; A61N 1/0539; A61N 2001/36039
  USPC .................. 600/372, 373, 377, 378, 544, 545; 606/129, 76; 607/116–118
  See application file for complete search history.

(56) References Cited

U.S. PATENT DOCUMENTS 2,458,305 A  *  1/1949  Sanders ........................ 604/526
3,847,687 A     11/1974  Davidsohn et al.

(Continued)

FOREIGN PATENT DOCUMENTS

WO     WO-0241666      5/2002
WO     WO-2006138358  12/2006

(Continued)

OTHER PUBLICATIONS

"International Application Serial No. PCT/IB06/53700, International Search Report mailed Nov. 21, 2008", 1 pg.

(Continued)

*Primary Examiner* — Lee S Cohen
*Assistant Examiner* — Erin M Cardinal
(74) *Attorney, Agent, or Firm* — Michael F. Scalise

(57) ABSTRACT

An apparatus comprising an electrode subsystem configured to interface to biological tissue, an electronic subsystem electrically coupled to the electrode subsystem by a connector, and a guide tube disposed over at least a portion of the electrode subsystem and the connector. The guide tube includes material to provide stiffness to the electrode subsystem and the connector in an axial direction of the guide tube. The guide tube material is removable from the electrode subsystem and the connector over the electronic subsystem when the electrode subsystem is positioned to interface to the biological tissue and while the electronic subsystem remains electrically coupled to the electrode subsystem.

17 Claims, 4 Drawing Sheets

(56) References Cited

U.S. PATENT DOCUMENTS

| | | | |
|---|---|---|---|
| 3,921,916 A | 11/1975 | Bassous | |
| 4,141,365 A | 2/1979 | Fischell et al. | |
| 4,166,469 A | 9/1979 | Littleford | |
| 4,306,562 A | 12/1981 | Osborne | |
| 4,455,192 A | 6/1984 | Tamai | |
| 4,461,304 A | 7/1984 | Kuperstein | |
| 4,465,482 A | 8/1984 | Tittel | |
| 4,762,135 A | 8/1988 | van der Puije | |
| 4,886,065 A | 12/1989 | Collins | |
| 4,904,237 A | 2/1990 | Janese | |
| 5,108,819 A | 4/1992 | Heller et al. | |
| 5,180,376 A | 1/1993 | Fischell | |
| 5,183,464 A * | 2/1993 | Dubrul et al. | 606/198 |
| 5,207,709 A | 5/1993 | Picha | |
| 5,215,088 A | 6/1993 | Normann et al. | |
| 5,308,442 A | 5/1994 | Taub et al. | |
| 5,322,064 A | 6/1994 | Lundquist | |
| 5,385,635 A | 1/1995 | O'Neill | |
| 5,390,671 A | 2/1995 | Lord et al. | |
| 5,395,349 A * | 3/1995 | Quiachon et al. | 604/248 |
| 5,409,469 A | 4/1995 | Schaerf | |
| 5,496,360 A | 3/1996 | Hoffmann et al. | |
| 5,515,848 A | 5/1996 | Corbett, III et al. | |
| 5,524,338 A | 6/1996 | Martynuik et al. | |
| 5,573,520 A | 11/1996 | Schwartz et al. | |
| 5,585,827 A | 12/1996 | Murakami | |
| 5,713,867 A * | 2/1998 | Morris | 604/164.05 |
| 5,720,099 A | 2/1998 | Parker et al. | |
| 5,744,958 A | 4/1998 | Werne | |
| 5,800,535 A | 9/1998 | Howard, III | |
| 5,843,150 A | 12/1998 | Dressen et al. | |
| 5,927,277 A | 7/1999 | Baudino et al. | |
| 5,938,694 A | 8/1999 | Jaraczewski et al. | |
| 5,975,085 A | 11/1999 | Rise | |
| 5,989,445 A | 11/1999 | Wise et al. | |
| 5,992,769 A | 11/1999 | Wise et al. | |
| 6,006,124 A | 12/1999 | Fischell et al. | |
| 6,016,449 A | 1/2000 | Fishell et al. | |
| 6,044,304 A | 3/2000 | Baudino | |
| 6,090,072 A * | 7/2000 | Kratoska et al. | 604/164.01 |
| 6,132,456 A | 10/2000 | Sommer et al. | |
| 6,181,569 B1 | 1/2001 | Chakravorty | |
| 6,205,361 B1 | 3/2001 | Kuzma et al. | |
| 6,228,111 B1 | 5/2001 | Tormala et al. | |
| 6,324,433 B1 | 11/2001 | Errico | |
| 6,325,797 B1 | 12/2001 | Stewart et al. | |
| 6,374,143 B1 | 4/2002 | Berrang et al. | |
| 6,430,443 B1 | 8/2002 | Karell | |
| 6,600,231 B2 | 7/2003 | Tominaga | |
| 6,618,623 B1 | 9/2003 | Pless et al. | |
| 6,749,600 B1 * | 6/2004 | Levy | 604/527 |
| 6,829,498 B2 | 12/2004 | Kipke et al. | |
| 6,834,200 B2 | 12/2004 | Moxon et al. | |
| 6,878,643 B2 | 4/2005 | Krulevitch et al. | |
| 6,939,327 B2 * | 9/2005 | Hall et al. | 604/164.05 |
| 7,004,948 B1 | 2/2006 | Pianca et al. | |
| 7,006,859 B1 | 2/2006 | Osorio et al. | |
| 7,010,356 B2 | 3/2006 | Jog et al. | |
| 7,011,680 B2 | 3/2006 | Alt | |
| 7,089,059 B1 | 8/2006 | Pless | |
| 7,181,288 B1 | 2/2007 | Rezai et al. | |
| 7,343,205 B1 | 3/2008 | Pianca et al. | |
| 7,449,011 B2 * | 11/2008 | Wenchell et al. | 604/164.01 |
| 7,548,775 B2 | 6/2009 | Kipke et al. | |
| 7,871,707 B2 | 1/2011 | Laude et al. | |
| 7,914,842 B1 | 3/2011 | Greenberg et al. | |
| 7,941,202 B2 | 5/2011 | Hetka et al. | |
| 8,012,127 B2 * | 9/2011 | Lieberman et al. | 604/160 |
| 8,224,417 B2 * | 7/2012 | Vetter | 600/378 |
| 2001/0049499 A1 | 12/2001 | Lui et al. | |
| 2002/0052610 A1 | 5/2002 | Skakoon et al. | |
| 2002/0183817 A1 | 12/2002 | Van Venrooij et al. | |
| 2002/0198446 A1 | 12/2002 | Hill et al. | |
| 2003/0004537 A1 * | 1/2003 | Boyle et al. | 606/200 |
| 2003/0093129 A1 | 5/2003 | Nicolelis et al. | |
| 2003/0100823 A1 | 5/2003 | Kipke et al. | |
| 2003/0114906 A1 | 6/2003 | Booker, III et al. | |
| 2003/0187459 A1 * | 10/2003 | Solar et al. | 606/129 |
| 2003/0187461 A1 | 10/2003 | Chin | |
| 2004/0006264 A1 | 1/2004 | Mojarradi et al. | |
| 2004/0102804 A1 * | 5/2004 | Chin | 606/190 |
| 2004/0102828 A1 | 5/2004 | Lowry et al. | |
| 2004/0106169 A1 | 6/2004 | Evans | |
| 2004/0199235 A1 | 10/2004 | Younis | |
| 2005/0004627 A1 | 1/2005 | Gibson et al. | |
| 2005/0021116 A1 | 1/2005 | He et al. | |
| 2005/0021117 A1 | 1/2005 | He et al. | |
| 2005/0125021 A1 * | 6/2005 | Nance et al. | 606/192 |
| 2005/0137647 A1 | 6/2005 | Wallace et al. | |
| 2005/0222647 A1 | 10/2005 | Wahlstrand et al. | |
| 2006/0122677 A1 | 6/2006 | Vardiman | |
| 2006/0173259 A1 * | 8/2006 | Flaherty et al. | 600/331 |
| 2006/0173263 A1 | 8/2006 | He et al. | |
| 2006/0200110 A1 * | 9/2006 | Lentz et al. | 604/524 |
| 2006/0247749 A1 | 11/2006 | Colvin | |
| 2006/0258951 A1 | 11/2006 | Bleich et al. | |
| 2007/0073130 A1 | 3/2007 | Finch et al. | |
| 2007/0135885 A1 | 6/2007 | Risi | |
| 2008/0132970 A1 | 6/2008 | Barolat | |
| 2008/0255439 A1 | 10/2008 | Tang et al. | |
| 2008/0262584 A1 | 10/2008 | Bottomley et al. | |
| 2009/0018631 A1 * | 1/2009 | Snoderly | 607/117 |
| 2009/0099555 A1 | 4/2009 | Viohl et al. | |
| 2009/0102068 A1 | 4/2009 | Pellinen et al. | |
| 2009/0118806 A1 | 5/2009 | Vetter et al. | |
| 2009/0132042 A1 | 5/2009 | Hetke et al. | |
| 2009/0149934 A1 | 6/2009 | Ameri et al. | |
| 2009/0171421 A1 | 7/2009 | Atalar et al. | |
| 2009/0234426 A1 | 9/2009 | Pellinen et al. | |
| 2009/0240314 A1 | 9/2009 | Kong et al. | |
| 2009/0248118 A1 | 10/2009 | Bradley et al. | |
| 2009/0253977 A1 | 10/2009 | Kipke et al. | |
| 2009/0299167 A1 | 12/2009 | Seymour | |
| 2009/0312770 A1 | 12/2009 | Kozai et al. | |
| 2010/0030298 A1 | 2/2010 | Martens et al. | |
| 2010/0145216 A1 | 6/2010 | He et al. | |
| 2010/0145422 A1 | 6/2010 | Seymour et al. | |
| 2011/0040257 A1 * | 2/2011 | Behymer et al. | 604/175 |
| 2011/0093052 A1 | 4/2011 | Anderson et al. | |
| 2011/0154655 A1 | 6/2011 | Hetke et al. | |
| 2011/0218549 A1 * | 9/2011 | Barker | 606/129 |

FOREIGN PATENT DOCUMENTS

| | | |
|---|---|---|
| WO | WO-2007042999 | 4/2007 |
| WO | WO-2007089738 | 8/2007 |
| WO | WO-2008011721 | 1/2008 |
| WO | WO-2008038208 | 4/2008 |
| WO | WO-2008072125 | 6/2008 |
| WO | 2008109298 | 9/2008 |
| WO | WO-2008109298 | 9/2008 |
| WO | WO-2009052423 | 4/2009 |
| WO | WO-2009052425 | 4/2009 |
| WO | WO-2011046665 | 4/2011 |
| WO | WO-2010057095 | 5/2012 |

OTHER PUBLICATIONS

"International Application Serial No. PCT/IB10/53250, International Search Report mailed Oct. 4, 2010", 3 pgs.

"International Application Serial No. PCT/US04/35030, International Search Report mailed Feb. 21, 2005", 2 pgs.

"International Application Serial No. PCT/US06/23139, International Search Report mailed Aug. 2, 2007", 1 pg.

"International Application Serial No. PCT/US07/02465, International Search Report mailed Feb. 13, 2008", 1 pg.

"International Application Serial No. PCT/US08/55025, International Search Report and Written Opinion mailed Oct. 27, 2008", 7 pgs.

"International Application Serial No. PCT/US08/80364, International Search Report and Written Opinion mailed Dec. 16, 2008", 5 pgs.

(56) References Cited

OTHER PUBLICATIONS

"International Application Serial No. PCT/US08/80366, International Search Report mailed Dec. 10, 2008", 6 pgs.

"International Application Serial No. PCT/US10/44167, International Search Report and Written Opinion mailed Sep. 27, 2010", 8 pgs.

"International Application Serial No. PCT/US2009/064591, International Search Report and Written Opinion mailed Jul. 21, 2010", 7 pgs.

Kaplan, W., et al., "A novel fabrication method of capillary tubes on quartz for chemical analysis applications", Proceedings, IEEE Workshop on Micro Electro Mechanical Systems, 1994, MEMS '94, (1994), 63-68.

Lin, L., et al., "Silicon-processed microneedles", Journal of Microelectromechanical Systems, 8(1), (1999), 78-84.

Seymour, John P, et al., "Neural probe design for reduced tissue encapsulation in CNS", Biomaterials, 28(25), (Sep. 2007), 3594-3607.

Seymour, John P., et al., "The insulation performance of reactive parylene films in implantable electronic devices", Biomaterials, 30(31), (Oct. 2009), 6158-6167.

* cited by examiner

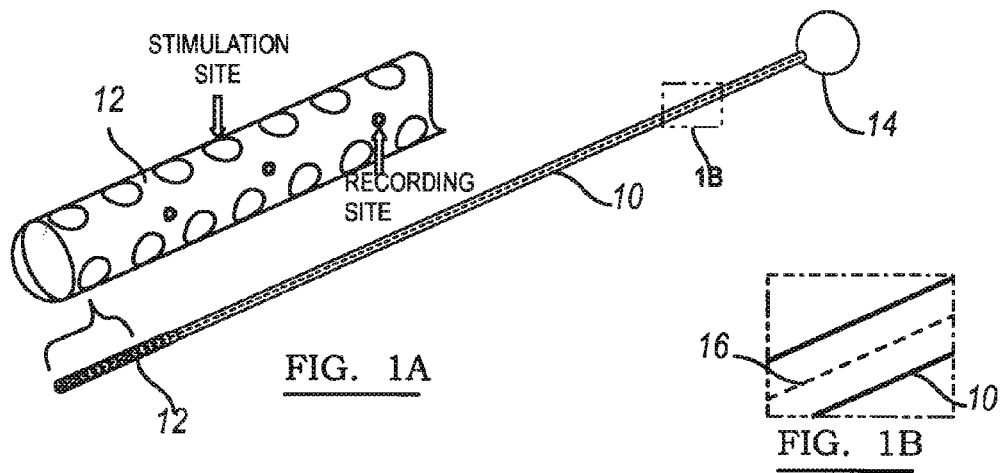
FIG. 1A
FIG. 1B
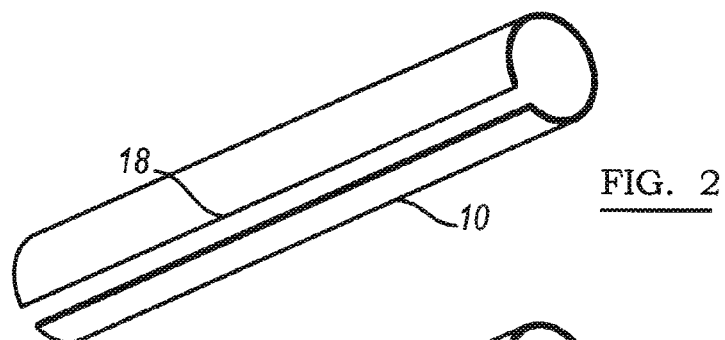
FIG. 2
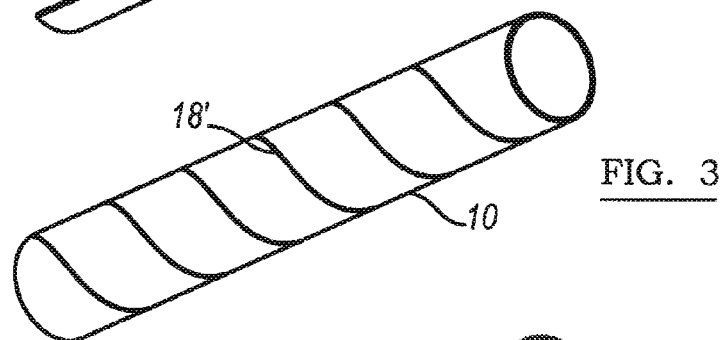
FIG. 3
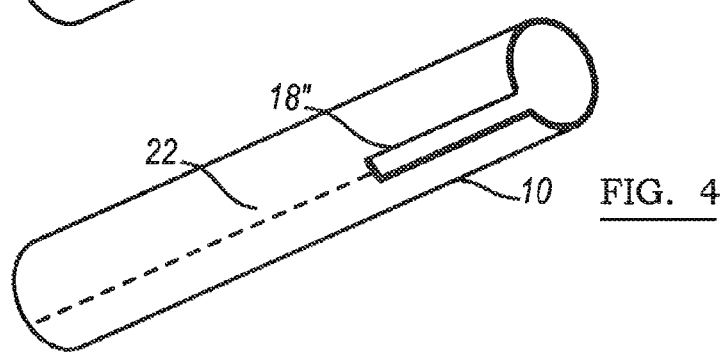
FIG. 4

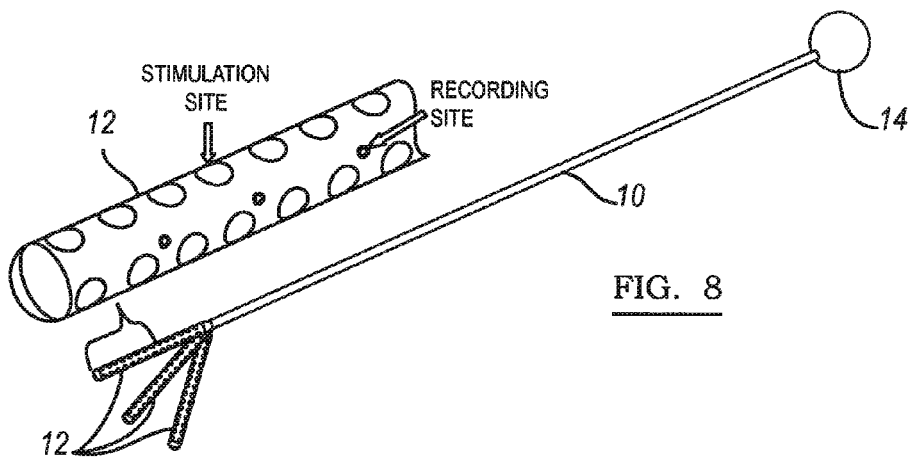
FIG. 8
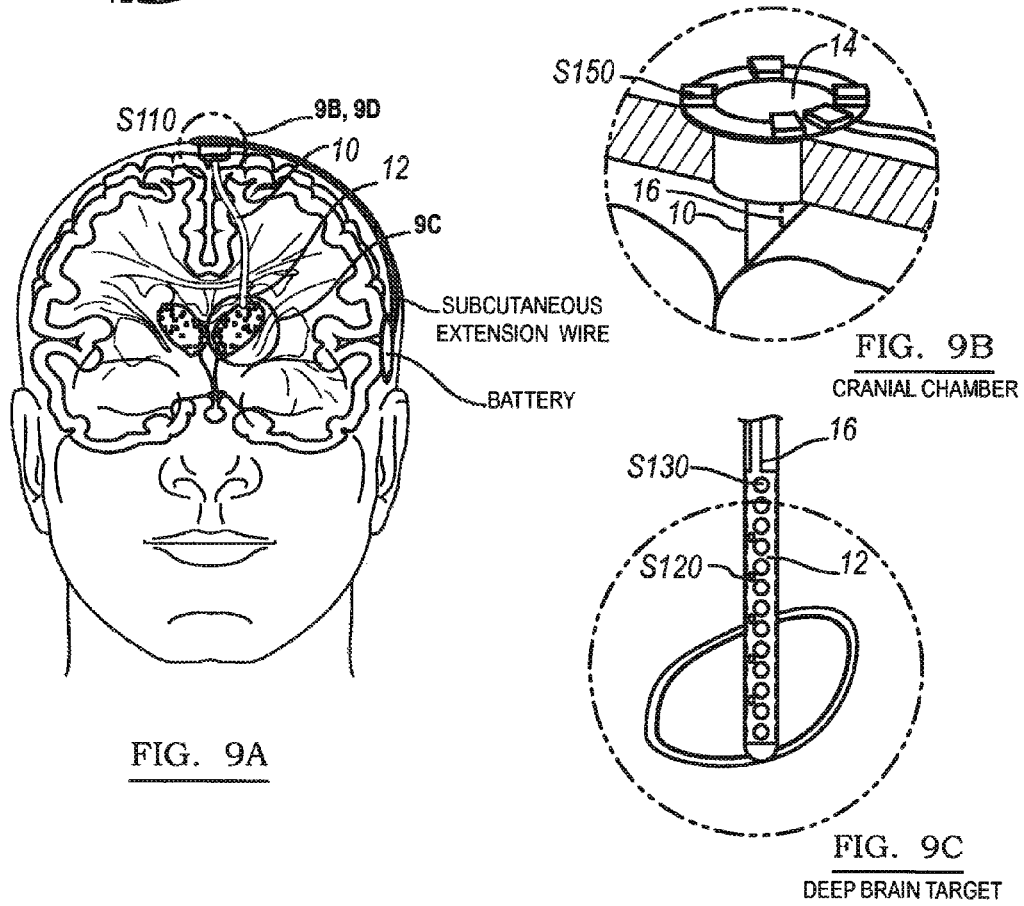
FIG. 9A
FIG. 9B
CRANIAL CHAMBER
FIG. 9C
DEEP BRAIN TARGET

CRANIAL CHAMBER

GUIDE TUBE FOR AN IMPLANTABLE DEVICE SYSTEM

CROSS-REFERENCE TO RELATED APPLICATIONS

This application is a continuation application of U.S. patent application Ser. No. 12/253,796, filed Oct. 17, 2008, now U.S. Pat. No. 8,224,417,which claims the benefit of priority under 35 U.S.C. §119(e) to U.S. Provisional Application No. 60/980,650, filed 17 Oct. 2007, entitled "Guide Tube for an Implantable Device System," each of which is incorporated in its entirety by this reference, and the priority of each of which is claimed herein.

This application is related to U.S. Patent Application Publication No. 2008/0208283, published on Aug. 28, 2008, and entitled "Neural Interface System," which is incorporated in its entirety by this reference.

TECHNICAL FIELD

This invention relates generally to the implantable device field, and more specifically to an improved guide tube of an implantable device.

BACKGROUND

Conventional microfabricated electrode arrays by themselves are often not mechanically robust enough to be inserted into tissue. Therefore, they must be coupled to a guide tube that is strong enough to maintain a straight trajectory and resist buckling while being inserted into tissue. The electrode arrays are generally coupled to electrical subsystems that are larger than the diameter of the guide tube. Thus, in order to remove a conventional guide tube while maintaining the position of the implanted electrode array, the electrical subsystem must be decoupled from the electrode array and the guide tube is slid off. Decoupling and recoupling the electrical subsystem can be challenging, and any recoupling is potentially exposed to fluids and thus subject to electrical shorting, leading to failure. Thus, there is a need for an improved guide tube that is removable from the implantable device without decoupling the electrical subsystem from the microfabricated electrode arrays. This invention provides such an improved and useful guide tube.

BRIEF DESCRIPTION OF THE FIGURES

FIG. 1A is a schematic drawing of the system of the first preferred embodiment of the invention.

FIG. 1B is an enlarged view of the area designated 1B in FIG. 1A.

FIGS. 2-7 are schematic drawings of several variations of the guide tube of the system.

FIG. 8 is a schematic drawing of a second preferred embodiment of the invention.

FIG.9A is a schematic drawing of the system implanted in a patient.

FIG. 9B is an enlarged view of the area indicated as 9B in FIG. 9A.

FIG. 9C is an enlarged view of the area indicated as 9C in FIG. 9A.

DESCRIPTION OF THE PREFERRED EMBODIMENTS

Figure 5:
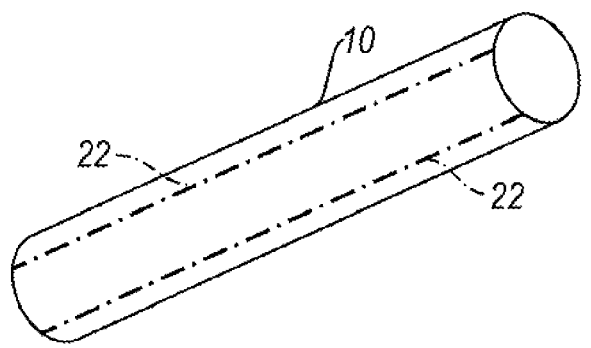

The following description of preferred embodiments of the invention is not intended to limit the invention to these embodiments, but rather to enable any person skilled in the art to make and use this invention.

As shown in FIG. 1, the implantable device system of the preferred embodiments includes a guide tube 10, a first electrical subsystem 12, and a second electrical subsystem 14. The first electrical subsystem 12 is connected to the second electrical subsystem 14. The guide tube 10 functions to facilitate the insertion of at least one first electrical subsystem 12 into tissue by preventing buckling and maintaining a generally straight trajectory through the tissue, functions to allow the first electrical subsystem(s) 12 to move freely with the tissue (i.e. not being rigidly constrained), and functions to allow the placement of the first electrical subsystem 12 without disconnecting the second electrical subsystem 14. The implantable device system may be implanted into the brain, spinal cord, peripheral nerve, muscle, or any other suitable anatomical location. The guide tube 10 of the system, however, may be alternatively used in any suitable environment and for any suitable reason.

1. The Guide Tube

The guide tube 10 of the preferred embodiments functions to facilitate the insertion of at least one first electrical subsystem 12, functions to allow the first electrical subsystem(s) 12 to move freely with the tissue (i.e. not being rigidly constrained), and functions to allow the placement of the first electrical subsystem 12 without disconnecting the second electrical subsystem 14. Therefore, the guide tube preferably operates in the following modes: active mode, during which the guide tube is rigid in the axial direction and facilitates insertion of the first electrical subsystem into tissue, and inactive mode, during which the guide tube allows the first electrical subsystem to move freely with the tissue.

The guide tube 10 is preferably made of a rigid material, which can be inserted into tissue or other substances without buckling and can maintain a generally straight trajectory through the tissue. The material may be uniformly rigid, or rigid only in a particular direction (such as the axial direction). The material is preferably plastic such as a medical grade plastic, but may alternatively be any suitable material such as metal or a combination of materials. The guide tube 10 may further include a sharpened end adapted to penetrate the tissue and aid in the insertion of the guide tube 10 into the tissue. The guide tube 10 may also include alignment and or fixation features to facilitate positioning and stabilizing the first electrical subsystem 12 in the tissue, particularly during removal of the guide tube.

The transition of the guide tube between active mode and inactive mode preferably occurs in one of several variations. In the first two variations, the guide tube 10 is adapted to be removable from the system of electrical subsystems. In another variation, the guide tube 10 is adapted to remain with the system of electrical subsystems. Although the guide tube 10 is preferably adapted in one of the several following variations, the guide tube 10 may be adapted in any suitable fashion or combination thereof to allow the transition of the guide tube between active mode and inactive mode such that the first electrical subsystem 12 to moves freely with the tissue, following the placement of the first electrical subsystem 12, without disconnecting the second electrical subsystem 14.

1.1 The Guide Tube Removed from a Portion of the System

As shown in FIG. 2, the guide tube 10 of the first variation defines a slit 18, which functions to allow the guide tube to be removed over a portion of the system. The slit 18 preferably does not prevent the guide tube 10 from maintaining rigidity as the guide tube 10 is inserted. Preferably a cable connecting the first electrical subsystem 12 and the second electrical subsystem 14 of the implantable device system slides through the slit 18, but any suitably thin portion of the implantable device system may slide through the slit 18. The slit preferably is a linear slit 18 or 18", as shown in FIGs. 2 and 4, respectively, which runs generally perpendicularly to the end of the guide tube. The slit may alternatively be a spiral slit 18', as shown in FIG. 3, and may run at any suitable angle to the end of the guide tube 10.

In a second version, as shown in FIGS. 4 and 5, the guide tube 10 may define a plurality of perforation lines 22, which function to allow the guide tube to be removed over a portion of the system. The perforation lines 22 may supplement or replace the slit 18 of the first variation. As the guide tube 10 is removed over a portion of the system, the portion of the system will apply a generally radial force to the guide tube 10, which will cause the perforation lines 22 to uncouple, creating an opening or a slit, and allow the guide tube 10 to be removed. There are preferably two axially extending perforation lines 22, such that the guide tube 10 is uncoupled into two portions. The two portions may be generally equal halves, or one portion may be larger than the other. Alternatively, there may be just one, or may be more than two perforation lines 22 uncoupling the guide tube 10. Additionally, the perforation lines 22 preferably run a portion of the guide tube 10 (as shown in FIG. 4), but may alternatively run the length of the guide tube 10 (as shown in FIG. 5). The perforation lines 22 are preferably linear and run generally perpendicularly to the end of the guide tube. The perforation lines 22 may alternatively be any suitable geometry and run at any suitable angle to the end of the guide tube 10.

In a third version, the guide tube 10 is made of a brittle material that functions to crack and widen as the guide tube is moved over a portion of the system. The brittle material will not prevent the guide tube 10 from maintaining rigidity as the guide tube 10 is inserted. The material is preferably adapted to crack in response to a force in the radial direction, while allowing the guide tube 10 to maintain rigidity in the axial direction. As the guide tube 10 is moved over a portion of the system, the portion of the system will apply a generally radial force to the guide tube 10, which will cause the material to crack, creating an opening or a slit, and allow the guide tube 10 to be removed. The guide tube 10 may be entirely made of the brittle material adapted to crack in response to a force in the radial direction and to rigid in the axial direction or a portion of the guide tube may be the brittle material while the remainder is conventional guide tube material. Preferably, the brittle material runs the length of the guide tube 10, but may alternatively run any suitable portion of the length of the guide tube 10. The portion of brittle material preferably runs generally perpendicularly to the end of the guide tube, but may alternatively be any suitable geometry and run at any suitable angle to the end of the guide tube 10.

1.2 The Guide Tube Removed Over the Second Electrical Subsystem

In a second variation, the guide tube 10 is adapted to break open, or at least expand its diameter to allow the removal of the guide tube 10 over the second electrical subsystem 14. The guide tube 10 is preferably adapted to break open, or at least expand its diameter in one of several versions.

The first three versions are similar to the first three versions of the first variation of the guide tube 10, as shown in FIGS. 2-5, except that the guide tube 10 is made from a material that can be opened or expanded in the radial direction to allow the guide tube 10 to be removed over the second electrical subsystem 14.

Figure 6:
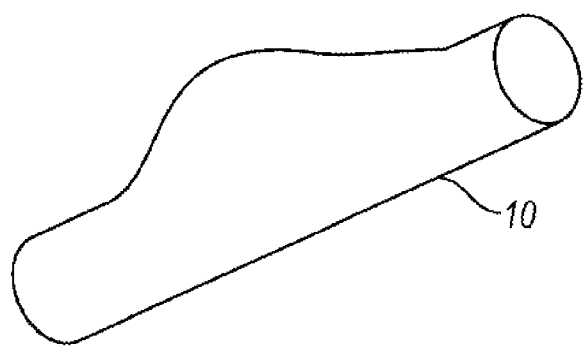

In a fourth version, as shown in FIG. 6, the guide tube 10 is preferably made of a flexible material that functions to widen as the guide tube is moved over the second electrical subsystem 14 of the system. The flexible material will not prevent the guide tube 10 from maintaining rigidity as the guide tube 10 is inserted. The material is preferably adapted to be flexible in the radial direction, while allowing the guide tube 10 to maintain rigidity in the axial direction. As the guide tube 10 is moved over a portion of the system, the portion of the system will apply a generally radial force to the guide tube 10, which will cause the material of the guide tube 10 to widen and allow the guide tube 10 to be removed. The guide tube 10 may be entirely made of an anisotropic material adapted to be flexible in the radial direction and rigid in the axial direction. A portion of the guide tube may be the anisotropic material while the remainder is conventional guide tube material, or a portion of the guide tube may be flexible material while the remainder is conventional guide tube material. Preferably, the flexible or partially flexible material runs the length of the guide tube 10, but may alternatively run any suitable portion of the length of the guide tube 10. The portion of flexible material preferably runs generally perpendicularly to the end of the guide tube, but may alternatively be any suitable geometry and run at any suitable angle to the end of the guide tube 10.

Figure 7:
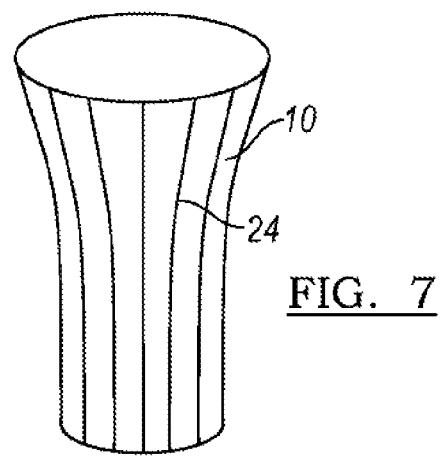

In a fifth version, as shown in FIG. 7, the guide tube 10 includes a flexible material and splines 24 that are rigid in the axial direction, which functions to widen as the guide tube is moved over a portion of the system. The splines 24 will allow the guide tube 10 to maintain rigidity as the guide tube 10 is inserted. As the guide tube 10 is moved over a portion of the system, the portion of the system will apply a generally radial force to the guide tube 10, which will cause the splines 24 to move apart and the material of the guide tube 10 to flex, widening the diameter of the guide tube 10, allowing the guide tube 10 to be removed. Alternatively, the guide tube 10 may include the splines 24 alone, and not further include a flexible material or only include the flexible material along a portion of the splines 24. The splines 24 are preferably strips of any suitable width and thickness and preferably run along the length of the guide tube 10 and run generally perpendicularly to the end of the guide tube. The splines 24 may alternatively be any suitable geometry, run any suitable portion of the length of the guide tube 10, and run at any suitable angle to the end of the guide tube 10. The splines 24 are preferably rigid, or may alternatively be flexible in the radial direction and rigid in the axial direction. The splines 24 may alternatively run circumferentially around the guide tube 10 or spiral around the guide tube 10, such that there are multiple circular splines, or a spring, stacked along the length of the guide tube. The circular splines preferably expand in the radial direction and due to the stacking, would be rigid in the axial direction.

1.3 The Guide Tube Adapted to Remain with the Electrical Subsystems

The guide tube 10 of the third variation is adapted to remain with the implanted system of electrical subsystems. The guide tube 10 is preferably adapted to be resorbable into the tissue after a period of time. The guide tube 10 in this variation is preferably made from a material that is resorbable such as polyglycolide or polylactide, but may alternatively be made from any suitable bioresorbable material.

In a second variation, as shown in FIG. 7, the guide tube 10 includes a flexible material and splines 24 that are rigid in the axial direction. The flexible material and splines 24 will not prevent the guide tube 10 from maintaining rigidity as the guide tube 10 is inserted. The splines 24 are preferably strips of any suitable width and thickness and preferably run along the length of the guide tube 10 and run generally perpendicularly to the end of the guide tube. The splines 24 are preferably rigid. The splines 24 may alternatively be any suitable geometry, run any suitable portion of the length of the guide tube 10, and run at any suitable angle to the end of the guide tube 10. The splines 24 may alternatively run circumferentially around the guide tube 10 or spiral around the guide tube 10, such that there are multiple circular splines 24, or a spring, stacked along the length of the guide tube. In this version, the flexible guide tube 10 may remain implanted, while the splines 24 are removed.

2. The Electrical Subsystems

The first electrical subsystem 12 of the preferred embodiments functions to interface with the tissue, or any other suitable substance, within which it has been implanted. The first electrical subsystem 12 may include multiple different electrical subsystems or a plurality of the same subsystems. As shown in FIG. 8, the first electrical subsystem 12 may include a plurality of electrical subsystems and the guide tube 10 may be adapted to guide multiple first electrical subsystems 12. The first electrical subsystem 12 is preferably at least one of several versions or any combination thereof.

In a first version, the first electrical subsystem 12 is a multi-banded cylindrical electrode with a linear arrangement of four equally spaced cylindrical electrodes, which can be used in monopolar or bipolar modes to deliver electrical stimulation to the surrounding tissue. The electrodes can deliver approximately spherical potential fields from separate locations along the cylindrical carrier.

In a second version, as shown in FIGS. 1 and 8, the first electrical subsystem 12 is a neural interface electrode array. The electrode array preferably has a plurality of electrode sites, and more preferably a plurality of electrode sites that is more than 4. The neural interface electrode array is adapted to provide dynamic tunable electrical stimulation ranging from stimulation with macroscale specificity to microscale directional patterning. The electrode array is preferably adapted to optimally sample (record) and/or selectively activate (stimulate) neural populations. The plurality of electrode sites can be tuned for recording, stimulation, or any combination thereof. Additionally, at least two electrode sites may be grouped to form a larger composite site that enables tuning the neural interface region for recording and/or stimulation. The neural interface electrode array is preferably made from a thin-film polymer substrate such that there is high density electrode sites at a first end of the array (the distal end) and bonding regions at a second end of the array (the proximal end). The polymer substrate is preferably parylene or some combination of parylene and inorganic dielectrics, but may alternatively be made out of any suitable material. The distal end of the array is preferably coupled to a carrier to provide structural support. The electrode array may further include fluidic channels providing the capability to deliver therapeutic drugs, drugs to inhibit biologic response to the implant, or any other suitable fluid.

The first electrical subsystem 12 may be adapted for long term implantation as in the first two variations, or alternatively may be adapted for short-term intraoperative use as in the following third variation. In the third version, the first electrical subsystem 12 is a mapping electrode system, which is adapted to perform clinical deep brain electrophysiological mapping for use in neurosurgerical applications. More specifically, the mapping electrode system is preferably adapted to perform simultaneous multichannel neural recording from precisely known locations along the deep microelectrode track. The mapping electrode may further have extended functionality such as multichannel recording and/or stimulation or fluid delivery.

Although the first electrical subsystem 12 is preferably one of these several versions, the first electrical subsystem 12 may be any suitable element or combination of elements to perform the desired functions.

The second electrical subsystem 14 of the preferred embodiments functions to operate with the first electrical subsystem 12. The second electrical subsystem 14 may include multiple different electrical subsystems or a plurality of the same subsystems. Additionally, the guide tube 10 may be adapted to be removable over multiple second electrical subsystems 14. The second electrical subsystem is preferably at least one of several versions or any combination thereof.

In a first version, as shown in FIG. 3, the second electrical subsystem 14 is a suitable electronic subsystem to operate with an implantable neural interface. The second electrical subsystem 14 may be a printed circuit board with or without on-board integrated circuits and/or on-chip circuitry for signal conditioning and/or stimulus generation, an Application Specific Integrated Circuit (ASIC), a multiplexer chip, a buffer amplifier, an electronics interface, an implantable pulse generator, an implantable rechargeable battery, integrated electronics for either real-time signal processing of the input (recorded) or output (stimulation) signals, integrated electronics for control of the fluidic components, any other suitable electrical subsystem, or any combination thereof. Although the second electrical subsystem 14 is preferably one of these several subsystems, the second electrical subsystem 14 may be any suitable element or combination of elements to operate any suitable first electrical subsystem 12.

The system may further include a connector such as a cable 16 that functions to couple the first electrical subsystem 12 to the second electrical subsystem 14. The cable 16 is preferably one of several versions. As shown in FIGS. 1 and 8, the cable is preferably a flexible ribbon cable. The ribbon cable is preferably a polymer ribbon cable, but may alternatively be any other suitable ribbon cable. The cable 16 may alternatively be any suitable element to couple the first electrical subsystem 12 to the second electrical subsystem 14, such as wires, conductive interconnects, etc. The ribbon cable may be encased in silicone or any other suitable material. In some situations, the electrical subsystem may have multiple ribbon cables. Preferably, multiple ribbon cables would be physically attached along their entire length, using a suitable adhesive such as medical grade adhesive or any other suitable connection mechanism. The cable is preferably connected to the electrical subsystems through ball bonds, ball bond, or any other suitable connection mechanisms. The cable 16 may alternatively be seamlessly manufactured with the first and or second electrical subsystem. The cable 16 may further include fluidic channels adapted to deliver therapeutic drugs, drugs to inhibit biologic response to the implant, or any other suitable fluid.

Figure 9D:
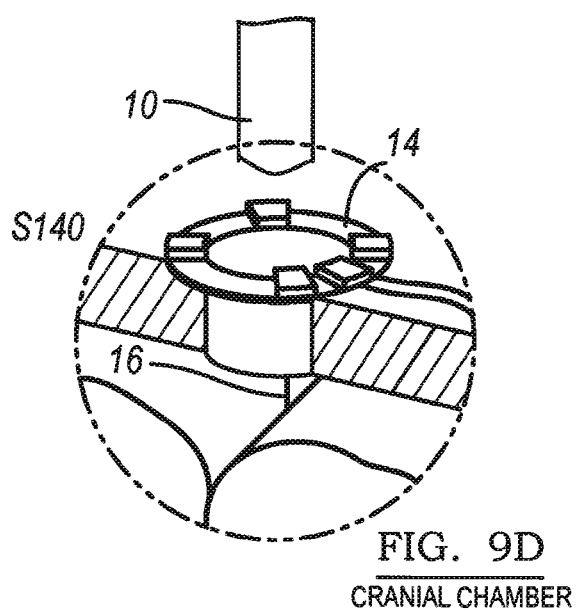
FIG. 9D is an enlarged view of the area indicated as 9D in FIG. 9A.

As shown in FIG. 9, a method of implanting an implant and its corresponding electrical components preferably includes any combination of the following steps (or any other suitable steps):

S110, which includes attaching a cranial chamber to the skull (preferably in a cranial burr-hole) of a patient (FIG. 9A);

S120, which includes implanting, through the guide tube 10, a first electrical subsystem 12 which is preferably a mapping electrode system (FIGS. 9B and 9C);

removing, through the guide tube 10, the mapping electrode system following microelectrode recording;

S230, which includes implanting, through the guide tube 10, a first electrical subsystem 12 which is preferably a neural interface electrode array coupled via a cable 16 to a second electrical subsystem 14 (FIGs. 9B and 9C);

S140, which includes removing the guide tube from the system (FIG. 9D);

S150, which includes placing the second electrical subsystem 14 within the chamber (FIG. 9B); and sealing the electrical subsystems within the chamber.

Although omitted for conciseness, the preferred embodiments include every combination and permutation of the various guide tubes 10, the various expansion elements, the various electrical subsystems, the various cables, and the various methods of use.

As a person skilled in the art will recognize from the previous detailed description and from the figures and claims, modifications and changes can be made to the preferred embodiments of the invention without departing from the scope of this invention defined in the following claim.

What is claimed is:

1. An implantable system, comprising:
   a) an electrode subsystem configured to interface with biological tissue;
   b) an electronic subsystem electrically coupled to the electrode subsystem by a connector; and
   c) a guide tube disposed over at least a portion of the electrode subsystem and at least a portion of the connector, the guide tube having a length extending in an axial direction and a width extending in a radial direction, wherein the guide tube comprises an anisotropic material that is rigid in the axial direction and expandable in the radial direction;
   d) at least one spiral spline removably disposed longitudinally in the guide tube, the at least one spline being rigid in the axial direction and flexible in the radial direction of the guide tube to thereby provide stiffness to the electrode subsystem and to the connector in the axial direction of the guide tube,
   e) wherein the guide tube is removable from the electrode subsystem, the connector, and the electronic subsystem with the guide tube remaining cohesive during such removal.

2. The system of claim 1 wherein the guide tube material is flexible.

3. The system of claim 1, wherein the connector includes a flexible ribbon cable.

4. The system of claim 1, wherein the electrode subsystem includes a plurality of electrodes adapted for recording neural activity.

5. The system of claim 4, wherein the electrodes are adapted by shape and size for deep brain. electrophysiological mapping.

6. The system of claim 4, wherein the connector includes a plurality of flexible ribbon cables to electrically couple the electrodes to the electronic subsystem.

7. The system of claim 4, wherein the plurality of electrodes are formed on a thin-film polymer substrate.

8. The system of claim 1, wherein the electronic subsystem is configured for placement in a cranial chamber.

9. The system of claim 1, wherein the connector includes a cable having fluidic channels formed therein.

10. A guide tube to facilitate insertion of an electrode subsystem and a connector into biological, tissue, the guide tube having a length extending in an axial direction and a width extending in a radial direction, the guide tube comprising:
    a) an anisotropic guide tube material that is rigid in the axial direction and flexible in the radial direction of the guide tube,
    b) at least one spline removably disposed longitudinally in the guide tube, the spline being rigid in the axial direction and flexible in the radial direction of the guide tube,
    c) wherein the guide tube material is expandable in the radial direction and remains cohesive in response to a force applied in the radial direction to effect removal of the guide tube from the electrode subsystem and the connector when the electrode subsystem is positioned to interface with the biological tissue.

11. The system of claim 10, wherein the at least one spline is a spiral spline that is disposed in the guide tube, wherein the spiral spline is rigid in the axial direction and flexible in the radial direction of the guide tube.

12. An implantable system, comprising:
    a) an electrode subsystem configured to interface with biological tissue;
    b) an electronic subsystem electrically coupled to the electrode subsystem by a connector; and
    c) a guide tube disposed over at least a portion of the electrode subsystem and at least a portion of the connector, the guide tube having a length extending in an axial direction and a width extending in a radial direction, wherein the guide tube comprises an anisotropic material that is rigid in the axial direction and expandable in the radial direction;
    d) at least one spline removably disposed longitudinally in the guide tube, the at least one spline being rigid in the axial direction and flexible in the radial direction of the guide tube to thereby provide stiffness to the electrode subsystem and to the connector in the axial direction of the guide tube,
    e) wherein the guide tube is removable from the electrode subsystem, the connector, and the electronic subsystem.

13. A guide tube having a length extending in an axial direction and a width extending in a radial direction, the guide tube comprising:
    a) an anisotropic material that is rigid in the axial direction and expandable in the radial direction;
    b) at least one spiral spline removably disposed longitudinally in the guide tube, the at least one spline being rigid in the axial direction and flexible in the radial direction of the guide tube to thereby provide stiffness in the axial direction of the guide tube,
    c) wherein the guide tube is removable from an implantable subsystem with the guide tube remaining cohesive during such removal.

14. A method comprising:
    a) electrically connecting an electrode subsystem to an electronic subsystem using a connector; and
    b) disposing a guide tube over at least a portion of the electrode subsystem and the connector, the guide tube having a length extending in an axial direction and a width extending in a radial direction, wherein the guide tube comprises an anisotropic material that is rigid in the axial direction and expandable in the radial direction;
    c) at least one longitudinally extending spline disposed in the guide tube, the at least one spline being rigid in the axial direction and flexible in the radial direction of the guide tube to thereby provide stiffness to the electrode subsystem and to the connector in an axial direction of the guide tube,
    d) wherein the guide tube material is removable from the electrode subsystem and from the connector over the electronic subsystem with the guide tube remaining cohesive during such removal when the electrode subsystem is positioned to interface with biological tissue and while the electronic subsystem remains electrically coupled to the electrode subsystem.

15. The method of claim 14 wherein the at least one spline disposed longitudinally in the guide tube is removable from the guide tube.

16. The method of claim 14 wherein the at least one spline is a spiral spline that is disposed in the guide tube, wherein the spiral spline is rigid in the axial direction and flexible in the radial direction of the guide tube.

17. The method of claim 14, wherein electrically connecting the electrode subsystem to the electronic subsystem using a connector includes connecting the electrode subsystem to the electronic subsystem using a flexible ribbon cable.

\* \* \* \* \*